United States Patent
Nakahata et al.

[11] Patent Number: 6,028,050
[45] Date of Patent: Feb. 22, 2000

[54] METHOD FOR INCREASING PLATELETS BY ADMINISTERING SOLUBLE INTERLEUKIN-6 RECEPTOR

[75] Inventors: Tatsutoshi Nakahata, Tokyo; Kiyoshi Yasukawa, Kawasaki, both of Japan

[73] Assignee: Tosoh Corporation, Yamaguchi, Japan

[21] Appl. No.: 08/979,303

[22] Filed: Nov. 26, 1997

[30] Foreign Application Priority Data

Nov. 27, 1996 [JP] Japan ................................ 8-316649

[51] Int. Cl.[7] .......................... A61K 38/17; A61K 38/19; A61K 38/20
[52] U.S. Cl. .................. 514/2; 514/8; 514/12; 514/885; 424/85.1; 424/85.2
[58] Field of Search ............... 514/2, 8, 12, 885; 424/85.1, 85.2

[56] References Cited

U.S. PATENT DOCUMENTS 5,462,731 10/1995 Aderka et al. ..................... 424/85.2

OTHER PUBLICATIONS

Shigetaka Asano, et al.; In Vivo Effects of Recombinant Human Interleukin–6 in Primates: Stimulated Production of Platelets; Blood, 75(8): 1602–1605 (1990).

Toshiyuki Ishibashi, et al.; Interleukin–6 Is a Potent Thrombopoetic Factor in Vivo in Mice; Blood, 74:(4):1241–1244 (1989).

Xingwei Sui, et al.; gp130 and c–Kit Signalings Synergize for ex vivo Expansion of Human Primitive Hemopoietic Progenitor Cells; Proc. Natl. Acad. Sci. USA 92:2859–2863 (1995).

Sakura Tajima, et al.; Analysis of Interleukin 6 Receptor and pg130 Expressions and Proliferative Capability of Human CD34+ Cells; J. Exp. Med. 184:1357–1364 (1996).

*Primary Examiner*—Prema Mertz
*Attorney, Agent, or Firm*—Howrey & Simon; Jeffrey I. Auerbach

[57] ABSTRACT

A platelet-increasing preparation which comprises an effective amount of an interleukin-6 receptor and a pharmaceutically acceptable excipient. Preferably the preparation further comprises interleukin-6 and an ingredient selected from a stem cell factor, interleukin-3 and thrombopoietin.

3 Claims, 1 Drawing Sheet

METHOD FOR INCREASING PLATELETS BY ADMINISTERING SOLUBLE INTERLEUKIN-6 RECEPTOR

BACKGROUND OF THE INVENTION (1) Field of the Invention

This invention relates to a platelet-increasing preparation comprising an interleukin-6 receptor, and a method of increasing platelets.

(2) Description of the Related Art

Interleukin-6 (abbreviated to "IL-6") is a lymphokine having an ability of increasing blood platelets. For example, it is reported in Ishibashi et al, Blood, vol. 74, p1241–1244 (1989) that administration of 5 μg/d of human recombinant IL-6, produced by *Escherichia coli*, to mice for consecutive 5 days reproducibly elevated platelet counts by approximately 50% to 60% of increase. It is further reported in Asano et al, Blood, vol. 75, p1602–1605 (1990) that administration of 5 to 80 μg/kg/d of the above human recombinant IL-6 to monkeys for consecutive 14 days caused dose-dependent increases in platelet count approximately twofold or more.

As seen from the above-cited reports, there is a demand of a method for increasing platelets by administration of human recombinant IL-6 and a platelet-increasing preparation comprising IL-6 as an effective ingredient, but a platelet-increasing preparation has not been developed yet at present.

IL-6 is bound to the surface of a target cell or to a soluble interleukin-6 receptor to stimulate gp130 protein on the target cell surface. Therefore, it is believed that, in order to increase platelet count by administration of human recombinant IL-6, it is essential that a certain number of IL-6 receptors are present on the surface of cell lines, which lead to production of platelets, such as multipotential stem cells or megakaryocytes, or a soluble IL-6 receptors are present at a certain concentration in blood or body fluid, whereby gp130 on the surface of cell lines is stimulated.

For example, in the case of human being, when a certain number of IL-6 receptors are not present on the surface of cell lines such as multipotential stem cells or megakaryocytes, and soluble IL-6 receptors are not present at a certain concentration in blood or body fluid, the platelet-increasing effect is not always obtained by administration of human IL-6, which is in contrast to the case of mice or monkeys.

SUMMARY OF THE INVENTION

In view of the foregoing, an object of the present invention to provide means for stimulating gp130 to increase platelet count by administration of an IL-6 receptor.

The inventors have studied the effect of an IL-6 receptor on the production of human megakaryocytes and found that IL-6 receptor enhances the ability of producing megakaryocytes in the co-presence of IL-6 by thrombopoietin (abbreviated to "TPO"), interleukin-3 (abbreviated to "IL-3") and stem cell factor (abbreviated to "SCF"). The inventors further have found that CD34 positive IL-6 receptor negative cells have an ability of producing megakaryocytes, but CD34 positive IL-6 receptor positive cells do not have an ability of producing megakaryocytes. The present invention has been completed based on these findings.

In accordance with the present invention, there is provided a platelet-increasing preparation comprising an interleukin-6 receptor as an effective ingredient and a pharmaceutically acceptable excipient.

Further, there is provided a method of increasing platelets which comprises administrating the preparation containing interleukin-6 receptor as an effective ingredient, to a patient in a dose of 1 to 50 μg of the active ingredient/kg/d.

DESCRIPTION OF THE PREFERRED EMBODIMENTS

Figure 1:
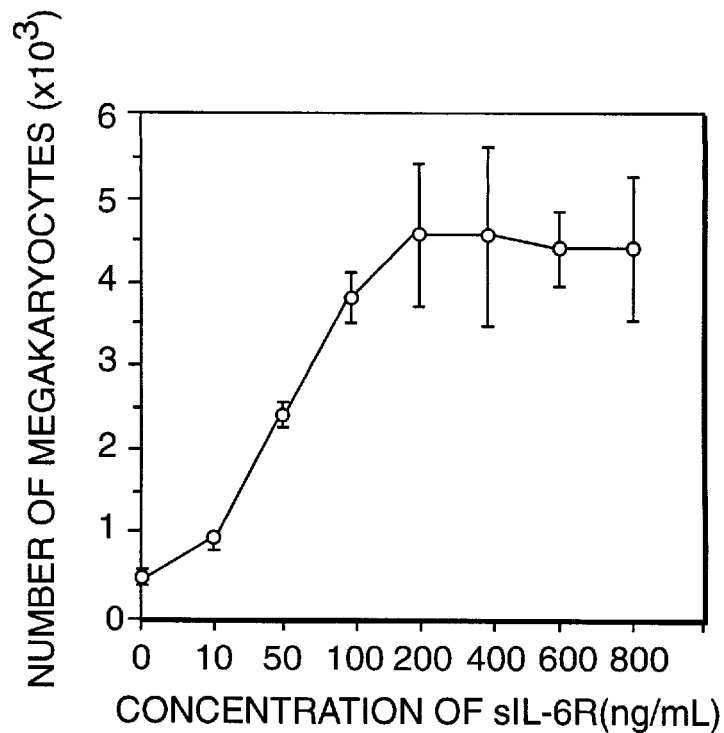
FIG. 1 is a diagram showing the effect of the concentration of an IL-6 receptor (abscissa) on the count of megakaryocytes (ordinate), as observed when CD34 positive cells were cultured according to the procedures described in Example 1.

An IL-6 receptor is a glycoprotein with a molecular weight of about 80,000 which has a transmembrane domain and an intracellular domain and is present in a membrane. When the IL-6 receptor is bound to IL-6, it is further bound to gp130 on a cell membrane to transmit a signal into the cell. Only an extracellular domain is necessary for the binding of IL-6 receptor to IL-6 and the binding thereof to gp130, and even a soluble IL-6 receptor having deleted therefrom a transmembrane domain and an intracellular domain is capable of being bound to IL-6 and further to gp130 to transmit a signal within a cell in a manner similar to the IL-6 receptor of a membrane type (complete length type) (see U.S. Pat. No. 5,171,840).

The IL-6 receptor used in the invention is not particularly limited and may be either soluble-type or complete length-type. More specifically, as examples of the IL-6 receptor used, there can be mentioned a soluble human recombinant IL-6 receptor described in Yasukawa et al, J. Biochem., vol. 108, p673–676 (1990), which consists of 344 amino acids in an extracellular domain (i.e., N-terminal residues of amino acids spanning from amino acid position 1 to amino acid position 344) and produced by a Chinese hamstar overay (CHO) cell; and a human recombinant IL-6 receptor described in Japanese Patent Application No. 7-330106, which is produced by Pichia yeast and has an extracellular domain (i.e., N-terminal residues of amino acids spanning from 114 position to 355 position).

IL-6 is a glycoprotein having a molecular weight of about 30,000, which is capable of being bound to an IL-6 receptor and further to gp130 on the cell surface to transmit a signal into the cell. Thus, it is preferable that the platelet-increasing preparation of the invention comprises IL-6 in addition to the IL-6 receptor, or IL-6 is administered in combination with the IL-6 receptor. The weight ratio of the IL-6 to IL-6 receptor is usually not larger than 10, preferably in the range of 0.1 to 10.

It is more preferable to incorporate, in the IL-6 receptor preparation, at least one ingredient selected from thrombopoietin (TPO), interleukin-3 (IL-3) and stem cell factor (SCF), in addition to the IL-6 receptor and IL-6. By the administration of these ingredients in combination with IL-6 receptor and IL-6, induction for the formation of megakaryocytes is drastically enhanced as shown in the working examples below. The weight ratio of TPO, IL-3 and/or SCF to the IL-6 receptor is usually not larger than 10, preferably in the range from 0.1 to 10.

Where the IL-6 receptor preparation is administered to the living body for enhancing the differentiation of stem cells to megakaryocytes, which finally differentiate into platelets, the intended induction for formation of megakaryocytes is believed to be attainable even when the preparation contains only IL-6 receptor as the acive ingredient. This is because, when IL-6 receptor is administered in a region where stem cells are present, such as marrow, the IL-6 receptor interacts with IL-6, SCF, IL-3 and/or TPO, which are also present within marrow or other regions.

As a preferable example of the IL-6 used in combination with the IL-6 receptor, there can be mentioned human recombinant IL-6 described in Tonouchi et al, J. Chem., vol. 104, p30–33 (1988) and in Yasukawa et al, Biochem. Lett., vol. 12, p419–424 (1990), which consists of 184 amino acids produced by *Escherichia coli.*

The platelet-increasing preparation of the invention is administered preferably parenterally, for example, by an intravenous, intramuscular or percutaneous administration. The dosage varies depending upon the particular kind of platelet-deficient diseases and the state of a patient, but the IL-6 receptor preparation is administered usually in a dose of 1 to 500 µg of the active ingredient/kg/day. The administration can be repeated according to the patient's progress toward recovery.

The platelet-increasing preparation is prepared by mixing the active ingredient together with an excipient. The excipient may be conventional and, for example, includes physiological saline, glucose solution, mannitol, methyl cellulose, human serum albumin and gelatin. The concentration of the IL-6 receptor in the preparation is usually at least 0.01% by weight based on the weight of the preparation. The upper limit of the concentration of the active ingredient is not particularly limited.

The platelet-increasing IL-6 receptor preparation can be lyophilized, and, immediately before the administration, the lyophilized preparation may be redissolved in an isotonic solution such as, for example, physiological saline, glucose solution or Ringer's solution.

The invention now will be specifically described by the following examples that by no means limit the scope of the invention.

EXAMPLE 1

Effect of IL-6 Receptor on Formation of Megakaryocytes (1)

Myeloid cells were collected by iliac puncture from a normal adult volunteer who gave an informed consent. Microphages were removed from the collected myeloid cells by using silica. Similarly microphages were removed from umbilical cord blood by using silica. Then, mononuclear cells were collected from each of the microphage-removed myeloid cells and the microphage-removed cord blood by a density gradient method using ficoll. The collected mononuclear cells were mixed together with magnetic beads having an anti-CD34 antibody bound thereto ("Dynabeads" M-450, supplied by Dynal Co.) in a proportion such that the number of cells and that of beads are equal, and the mixture was treated at 4° C. for 30 minutes. The thus-obtained beads having bound thereto CD34 positive cells were collected by using a magnet (magnetic particle concentrator, supplied by Dynal Co.), and the CD34 positive cells were separated from the beads by using DETACHa Bead CD34, supplied by Dynal Co.). The analysis using a cell sorter revealed that the thus-obtained fraction of CD34 positive cells had a purity of 85 to 95%. The two kinds of CD34 positive cells, one originating from cord blood and the other from myeloid, were tested for their capability of differentiating into megakaryocytes as follows.

(i) Differentiation of CD34 positive cells originating from cord blood

Using the thus-obtained CD34 positive cells originating from cord blood, a CD34 positive cell-containing a-medium was prepared, 1 ml of which contained 2,000 CD34 positive cells, and 2% of bovine serum albumin, 10 µg/ml of insulin, 200 µg/ml of transferrin, $1 \times 10^{-5}$M of 2-mercapto-ethanol, 40 µg/ml of low-density lipoprotein (supplied by Sigma Co.), 100 ng/ml of IL-6, 100 ng/ml ct SCF, and IL-6 receptor in a varied amount spanning from 0 to 200 ng/ml (shown in FIG. 1). The IL-6 receptor used was prepared according to the procedure described in Yasukawa et al, J. Biochem., vol. 108, p673–676 (1990). The culture was carried out by scattering 1 ml of the CD34 positive cell-containing medium in each well of a 24 well plate and maintaining the medium at 37° C. in an atmosphere consisting of 5% of $CO_2$, 5% of $O_2$ and 90% of $N_2$. One week after, a half of the liquid medium was removed and cells were collected therefrom.

The number of megakaryocytes in the collected cells was counted by an ordinary method using an anti-IIbIIIa antibody, described in Okumura et al, Blood, vol. 80, p642–647 (1992). The results are shown in FIG. 1, wherein the ordinate indicates the number of megakaryocytes ($\times 10^3$) and the abscissa indicates the concentration of soluble IL-6 receptor (ng/ml).

As seen from FIG. 1, the number of megakaryocytes was increased as an increase of the IL-6 receptor added. This means that an IL-6 receptor has a function of inducing differentiation of stem cells, derived from cord blood, to megakaryocytes in the co-presence of IL-6 and SCF.

(i) Differentiation of CD34 positive cells originating from myeloid

The above-mentioned differentiation procedure (i) was repeated wherein the CD34 positive cells originating from myeloid were used instead of the CD34 positive cells originating from cord blood. Similar results were obtained, namely, it was found that an IL-6 receptor had a function of inducing differentiation of stem cells, derived from myeloid, to megakaryocytes in the co-presence of IL-6 and SCF.

EXAMPLE 2

Effect of IL-6 Receptor on Formation of Megakaryocytes (2)

Using the CD34 positive cells originating from umbilical cord blood, a CD34 positive cell-containing α-medium was prepared, 1 ml of which contained 2,000 CD34 positive cells, and 2% of bovine serum albumin, 10 µg/ml of insulin, 200 µg/ml of transferrin, $1 \times 10^{-5}$M of 2-mercapto-ethanol, 40 µg/ml of low-density lipoprotein (supplied by Sigma Co.), and one or more of the following factors:

(i) 200 U/ml of IL-3,
(ii) 100 ng/ml of SCF,
(iii) 100 ng/ml of IL-6,
(iv) 200 ng/ml of IL-6 receptor, and
(v) 4 U/ml of TPO.

Culture was carried out by scattering 1 ml of the CD34 positive cell-containing medium in each well of a 24 well plate and maintaining the medium at 37° C. in an atmosphere consisting of 5% of $CO_2$, 5% of $O_2$ and 90% of $N_2$. One week after, a half of the liquid medium was removed and cells were collected therefrom. The number of megakaryocytes in the collected cells was counted by the same method (using an anti-IIbIIIa antibody) as employed in Example 1. The results (culture for 7 days) are shown in Table 1.

To the residual half of the liquid medium, a fresh medium having the same composition as used above was added, and the culture was continued for further one week. The number of megakaryocytes in a collected cells was counted by the same way as mentioned above. The results (culture for 14 days) are shown in Table 1.

Each of the above procedures was repeated three times, and the results were expressed in terms of "the average number of megakaryocytes ± the standard deviation (SD) value" in Table 1. "%" in the column of positive cell number means the proportion (in %) of the number of megakaryocytes produced to the total number of cells in each medium.

As seen from Table 1, IL-6 receptor exhibited an enhanced capability of inducing the formation of megakaryocytes in the copresence of IL-6 and SCF; IL-3 and IL-6; or TPO and IL-6. Asterisked mediums exhibited that there was a statistically significant difference (significance level P<0.005–0.0001) between the data obtained in a medium containing the soluble IL-6 receptor and the data obtained in a medium not containing the soluble IL-6 receptor.

TABLE 1

| | | 7 days after Positive Cell No. | | 14 days after Positive Cell No. | |
|---|---|---|---|---|---|
| | Factor | ×10³ | % | ×10³ | % |
| 1 | sIL-6R + IL-6 | 0 | 0 | 0 | 0 |
| 2 | SCF | 0 | 0 | 0 | 0 |
| 3 | IL-6 + SCF | 0.33 ± 0.04 | 0.8 | 2.32 ± 2.05 | 2.4 |
| 4* | sIL-6R + IL-6 + SCF | 4.29 ± 0.46 | 5.0 | 91.59 ± 25.38 | 6.5 |
| 5 | IL-3 | 0.08 ± 0.02 | 1.3 | 0.93 ± 0.29 | 7.0 |
| 6 | IL-6 + IL-3 | 0.22 ± 0.01 | 1.3 | 7.14 ± 0.76 | 18.8 |
| 7* | sIL-6R + IL-6 + IL-3 | 2.93 ± 1.91 | 11.5 | 27.00 ± 10.20 | 36.4 |
| 8 | TPO | 2.33 ± 1.00 | 22.0 | 50.60 ± 49.00 | 98.0 |
| 9 | IL-6 + TPO | 2.45 ± 1.20 | 23.0 | 51.30 ± 21.00 | 95.6 |
| 10* | sIL-6R + IL-6 + TPO | 5.00 ± 1.26 | 21.0 | 144.00 ± 135.59 | 90.5 |
| 11 | TPO + SCF | 44.90 ± 30.10 | 55.0 | 445.00 ± 35.45 | 49.5 |
| 12 | TPO + IL-3 | 2.49 ± 1.20 | 14.2 | 69.87 ± 15.60 | 82.2 |

Note, sIL-6R: soluble interleukin-6 receptor

EXAMPLE 3

Effect of IL-6 Receptor on Formation of Megakaryocytes (3)

Culture using a methyl cellulose-containing medium was conducted according to the procedures described in Nishi et al, Blood, vol. 76, p1330- (1990); Tanaka et al, Blood, vol. 80, p1743- (1992); and Koike et al, J. Exp. Med., vol. 166, p879- (1988).

Using the fraction of CD34 positive cells, obtained in Example 1, a CD34 positive cell-containing a-medium was prepared, 1 ml of which contained 500 CD34 positive cells, and 0.9% of methyl cellulose, 2% of bovine serum albumin, 300 pg/ml of transfferin, 160 µg/ml of lecithin (supplied by Sigma Co.), 96 µg/ml of cholesterol (supplied by Nakarai Co.), 10 µg/ml of insulin, $5\times10^{-5}$M of 2-mercaptoethanol, and one or more of the factors recited in Example 2 (the concentrations of the factors were the same as those described in Example 2). 1 ml of each of the CD34 positive cell-containing mediums was scattered in a Petri dish having a diameter of 35 mm and the culture was conducted at 37° C. in an atmosphere consisting of 5% of $CO_2$, 5% of $O_2$ and 90% of $N_2$. One week after and two weeks after the commencement of culture, the medium was observed by a microscope to count the number of CFU-Mk (colony containing at least 4 but fewer than 50 megakaryocytes), the number of BFU-Mk (colony containing at least 60 megakaryocytes) and the number of Mk-mix (colony containing not only megakaryocytes but also other cells such as granulocytes and macrophages). The results are shown in Table 2.

Each of the above procedures was repeated three times, and the results were expressed in terms of "the average number of colonies ± the standard deviation (SD) value" in Table 2.

TABLE 2

| | Number of colonies per 500 cells | | | |
|---|---|---|---|---|
| Factor | CFU-Mk | BFU-Mk | Mk-mix | Total |
| 3 IL-6 + SCF | 1.0 ± 1.5 | 0 | 0 | 1.0 ± 1.5 |
| 4 sIL-6R + IL-6 + SCF | 9.7 ± 4.2* | 3.3 ± 1.5 | 22.7 ± 3.5 | 35.7 ± 6.5* |
| 5 IL-3 | 2.7 ± 1.2 | 0 | 0 | 2.7 ± 1.2 |
| 6 IL-6 + IL-3 | 3.7 ± 0.6 | 0.3 ± 0.6 | 2.0 ± 1.0 | 6.0 ± 1.0 |
| 7 sIL-6R + IL-6 + IL-3 | 4.7 ± 1.2 | 1.7 ± 1.6* | 4.3 ± 1.5 | 10.7 ± 2.9* |
| 8 TPO | 24.0 ± 3.6 | 1.3 ± 1.5 | 0 | 25.3 ± 3.1 |
| 9 IL-6 + TPO | 26.0 ± 5.3 | 2.0 ± 1.5 | 0 | 27.1 ± 2.6 |
| 10 sIL-6R + IL-6 + TPO | 27.3 ± 2.1 | 6.0 ± 1.6* | 0 | 33.3 ± 2.8* |
| 11 TPO + SCF | 32.0 ± 7.0 | 17.7 ± 6.4 | 1.6 ± 1.5 | 51.3 ± 13.7 |
| 12 TPO + IL-3 | 31.0 ± 2.6 | 10.3 ± 2.3 | 53.0 ± 3.0 | 94.0 ± 4.0 |

Run numbers correspond to those in Table 1.

As seen from Table 2, IL-6 receptor exhibited an enhanced capability of inducing the formation of megakaryocytes in the copresence of IL-6 and SCF; or IL-3 and IL-6; or TPO and IL-6. Asterisked mediums exhibited that there was a statistically significant difference (significance level P<0.005–0.0001) between the data obtained in a medium containing the soluble IL-6 receptor and the data obtained in a medium not containing the soluble IL-receptor.

EXAMPLE 4

Effect of IL-6 Receptor on Formation of Megakaryocytes (4)

The effect of CD34 positive cells' having a capability of differentiating to megakaryocytes, on development of IL-6 receptor was examined as follows.

A fraction of CD34 positive IL-6 receptor negative cells and a fraction of CD34 positive IL-6 receptor positive cells were separately prepared by fractionation using a sorter. From each of the CD34 positive IL-6 receptor negative cells and CD34 positive IL-6 receptor positive cells, a CD34 positive IL-6 receptor positive (or negative) cell-containing α-medium was prepared, 1 ml of which contained 2,000 CD34 IL-6 receptor positive (or negative) cells, and 2% of bovine serum albumin, 10 µg/ml of insulin, 200 µg/ml of transferrin, $1\times10^{-5}$M of 2-mercapto-ethanol, 40 µg/ml of low-density lipoprotein (supplied by Sigma Co.), and two or three of the following factors:

(i) 200 U/ml of IL-3,
(ii) 100 ng/ml of SCF,
(iii) 100 ng/ml of IL-6,
(iv) 200 ng/ml of IL-6 receptor, and
(v) 4U/ml of TPO.

Culture was carried out by scattering 1 ml of the CD34 positive IL-6 receptor positive (or negative) cell-containing medium in each well of a 24 well plate and maintaining the medium at 37° C. in an atmosphere containing 5% of $CO_2$, 5% of $O_2$ and 90% of $N_2$. One week after, a half of the liquid medium was removed and cells were collected therefrom.

The number of megakaryocytes in the collected cells was counted by the same method (using anti-IIbIIIa antibody) as employed in Example 1. The results are shown in a histogram of FIG. 2, wherein the ordinate indicates the number of megakaryocytes ($\times 10^3$), and black bars are concered with the experiments using the CD34 positive IL-6 receptor negative cells and hatched bars are concerned with the experiments using the CD34 positive IL-6 receptor negative cells. (a), (b) and (c) are concerned with the experiments using the mediums containing the following factors.

(a) SCF+IL-6
(b) SCF+IL-6+sIL-6R
(c) sIL-6R+IL-6+TPO

Figure 2:
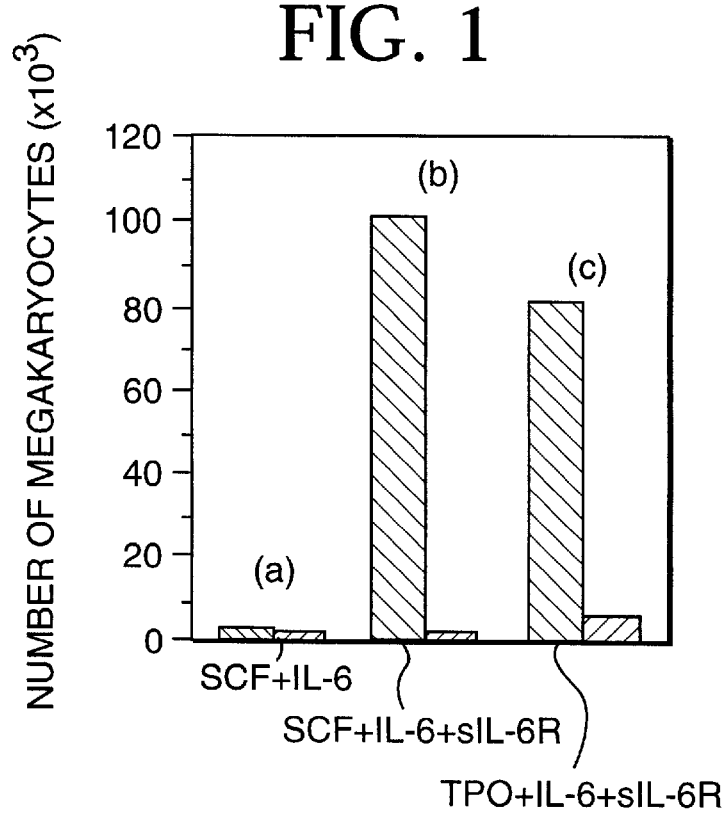
FIG. 2 is a histogram showing the count of megakaryocytes as observed when CD34 positive IL-6 receptor positive cells or CD34 positive IL-6 receptor negative cells were cultured according to the procedures described in Example 4, wherein black bars and hatched bars correspond to the results obtained when CD34 positive IL-6 receptor negative cells and CD34 positive IL-6 receptor positive cells were cultured, respectively.

As seen from FIG. 2, the CD34 positive IL-6 receptor negative cells exhibited a capability of differentiating to megakaryocytes in the presence of IL-6 receptor, IL-6 and SCF; or IL-6 and TPO. The CD34 positive IL-6 receptor positive cells did not exhibit a capability of differentiating to megakaryocytes under the same conditions. Thus, CD34 positive cells which are capable of differentiating to megakaryocytes are not IL-6 receptor positive cells, but IL-6 receptor negative cells. This shows that an IL-6 receptor is indispensable for increasing platelets.

In accordance with the present invention, there are provided novel medicine and therapy for patients suffering from a disease caused by decrease of platelets, or patients suffering from platelet-decrease caused during the course of therapy for a disease. It would be expected to cure or relieve a cancer by treating with chemotherapy or radio-therapy in combination with administration of the platelet-increasing preparation of the invention.

What is claimed is:

1. A method of increasing platelets in a patient in need of such increase, which comprises administering a preparation comprising an effective amount of a soluble interleukin-6 receptor and a pharmaceutically acceptable excipient, to the patient in a dosage of 1 to 500 $\mu$g of the active ingredient/kg/d.

2. The method of increasing platelets in a patient according to claim 1, wherein the preparation further comprises interleukin-6.

3. The method of increasing platelets in a patient according to claim 2, wherein the preparation further comprises at least one ingredient selected from the group consisting of a stem cell factor, interleukin-3 and thrombopoietin.

* * * * *